United States Patent [19]

Gold

[11] 4,065,675

[45] Dec. 27, 1977

[54] FLOW MONITORING DEVICES

[75] Inventor: Roy Charles Gold, London, England

[73] Assignee: The British Petroleum Company Limited, Sunbury-on-Thames, England

[21] Appl. No.: 692,388

[22] Filed: June 3, 1976

[30] Foreign Application Priority Data

June 11, 1975 United Kingdom ............ 25004/75

[51] Int. Cl.² ............ G01N 21/26; G08B 21/00
[52] U.S. Cl. ............ 250/576; 307/118; 340/239 R; 356/181
[58] Field of Search ............ 116/117 R, 112, 109; 73/421 R, 290 V; 141/95, 192, 198; 340/8 R, 239 R, 222, 244 R; 141/198; 356/181; 250/576; 307/118

[56] References Cited

U.S. PATENT DOCUMENTS

| 2,523,363 | 9/1950 | Gehman | 141/198 X |
|---|---|---|---|
| 2,660,063 | 11/1953 | Sawers | 73/425.4 R |
| 2,831,452 | 4/1958 | Haynes | 141/95 X |
| 3,213,438 | 10/1965 | Felice et al. | 340/244 R |
| 3,274,539 | 9/1966 | Sykes | 340/8 R |
| 3,441,637 | 4/1969 | Topol | 340/244 R |
| 3,550,651 | 12/1970 | McKellen et al. | 141/198 |
| 3,636,360 | 1/1972 | Oishi et al. | 73/293 X |
| 3,844,171 | 10/1974 | Rodger | 73/293 |
| 3,898,637 | 8/1975 | Wolstenholme | 340/239 R |

OTHER PUBLICATIONS

Publ., "Sonac. New Ultrasonic . . . System," Delavan Mfg. Co., Bulletin 41-42, Nov. 1962, 6 pages.

Primary Examiner—Daniel M. Yasich
Attorney, Agent, or Firm—Brooks, Haidt, Haffner & Delahunty

[57] ABSTRACT

This invention relates to a liquid flow monitoring device which uses a probe comprising an energy transmitter spaced apart from an energy receiver such that the bridging of the gap between the transmitter and receiver by flowing liquid emits a signal.

5 Claims, 2 Drawing Figures

FLOW MONITORING DEVICES

The present invention relates to a flow monitoring device and particularly to a device for monitoring pulse flow of liquids.

Conventional devices available for automatically extracting representative samples of a liquid, such as crude oil, flowing through pipe-lines or other source suffer from the limitation that there is no provision for obtaining confirmation at a local or remote point that the extracted sample is actually being collected in a container neither do they have a facility to detect when the container is full.

It has now been found that both these objectives, especially the one relating to the continuous monitoring of flow, may be achieved by a single device incorporated in an automatic sampler or other apparatus where monitoring of pulse flow is desirable.

Accordingly, the present invention is a liquid flow monitoring device comprising a chamber having an inlet and an outlet and containing a probe comprising an energy transmitter spaced apart from an energy receiver, the probe being positioned relative to the inlet such that liquid entering the chamber bridges the space between the transmitter and the receiver thereby activating the probe to emit a signal.

The probe is preferably fork-shaped with two substantially parallel prongs. One of the prongs is provided with the transmitter and the other with the receiver. Bridging the gap between these prongs of the fork, e.g. by the liquid being monitored, triggers off an electrical signal which may be connected to an audio and/or visual alarm. The dimensions and shape of the inlet and of the probe may be designed to suit the particular type of liquid being sampled. This can be determined by prior knowledge of the approximate viscosity of liquid to be sampled. If the type of probe described above is used, the inlet delivering the grab sample is provided with a shaped orifice and positioned with respect to the prongs of the fork such that the discharge of the sample bridges the gap between the prongs, thus triggering off an electrical signal indicating that liquid is flowing. The nature of the transmitter and the receiver of the probe would also depend upon the type of liquid being monitored. For example, for some suitable liquids the detector probe may be an optical probe with photo-electric cells functioning as transmitter and receiver. On the other hand, for other liquids, particularly those which are highly viscous and opaque, it may be preferable to use an ultrasonic probe for monitoring the flow. For other applications devices such as thermistors based on thermal conductivity principles, and capacitives measuring change in dielectric constant may be used, though a broader interpretation of the terms "energy transmitter" and "energy receiver" would be necessary.

The orientation of the probe in the device is such that the grab sample being discharged into the chamber falls freely under gravity through the space which is quickly re-established when the liquid ceases to flow. The discharged liquid may be collected in the chamber or in a suitable container.

The signals from the probe may be amplified by the control unit to actuate a relay which can operate pumps, valves, indicators, controllers, counting devices, alarms or other machinery or recording or control instrumentation.

The chamber may be made of a metal such as stainless steel or of suitable synthetic materials such as nylon or polytetrafluoroethane. The chamber may be provided with a suitable relief valve to relieve pressure build-up in the collecting container. The probe may be mounted in the chamber by means of matching screw threads so that the probe may be screwed in a vertical position within the chamber with the point of detection facing downwards in the direction of the flow of the liquid through the cell.

Although it is conceivable to make the chamber in the device as a single integral unit, for the sake of convenience during cleaning or changing of probes, it is preferable to have a unit with an upper half containing the inlet detachable from a lower half containing the outlet. This may be achieved by providing both the upper and lower parts of the cell with matching screw threads. Alternatively, it could take the form of a sleeve with suitable liquid-tight seals. The entire device is preferably adapted to be mounted within or to form the sealing cap of a sample container.

The automatic samplers envisaged under the present invention are those which contain a sampling valve which may be internal or external to the product line, which valve is opened and closed automatically, for example, using a solenoid valve actuated by an electrical signal. The sample from such automatic samplers may be obtained repetitively either at variable frequency and line flow rate or by keeping the frequency of the opening constant but making the duration of the opening of the valve proportional to the line flow rate. Whichever technique is used, the impulses from the flow monitoring device of the present invention may be used to provide evidence that discrete samples are being obtained from the sampler. For example, the electronic circuits associated with the sample detector may be arranged to provide an electrical signal which can be used to create an alarm condition should sample liquid fail to bridge the space between the receiver and the transmitter within an appropriate period after a "sample grab" signal is received from the automatic sampler control unit. This may be followed by using the "sample flowing" signal to cancel an "alarm pending" device set up by the initial "sample grab" signal. If the liquid fails to flow after the appropriate delay period then, having remained uncancelled, the alarm condition will proceed. Since the sample flowing signal is normally an intermittent one which is present only when a grab is being taken, appropriate electronic circuits may be arranged to give indication of a full container when the liquid reaches a level such that the space between the transmitter and receiver is continually bridged.

The "sample flowing" signals may be accumulated in a counting system to give continuous indication of the increasing level of sample in the collecing container and at a pre-set number of counts representing a desired level or an elasped time period may be used to initiate devices to divert the flow of sample into an alternative container.

The invention in one of its embodiments is further illustrated with reference to the drawings.

Figure 1:
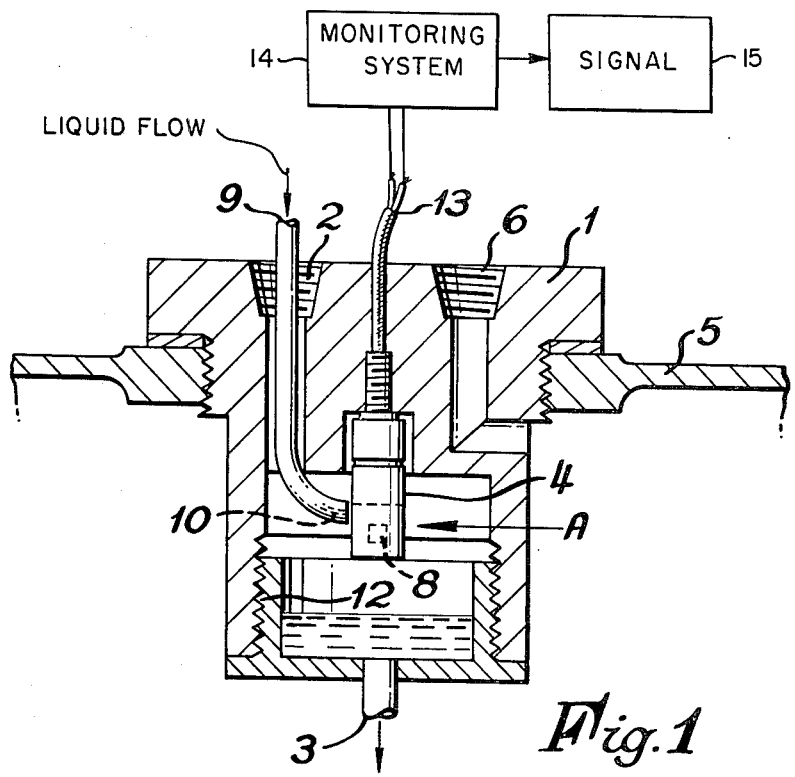
FIG. 1 shows a sectional view of the device.

In FIG. 1 the device 1 is fitted as a sealing cap for the sample container 5. The device 1 is provided with an inlet 2, an outlet 3, an ultrasonic detector probe 4 and a relief valve 6. The outlet 3 is part of a detachable lower part of the device 1 screwed on at 12. The ultrasonic probe has two prongs provided respectively with a receiver crystal 8 and an ultrasonic crystal transmitter 7. The two prongs form a gap 11 through which a "grab sample" is delivered to the cell via the orifice 10 of the delivery tube 9 connected to the pipeline (not show). Leads 13 connect the ultrasonic probe to an electronic monitoring system 14, responsive to electrical signals from the probe. The monitoring system is used to activate signal or alarm 15.

Circuitry for the above system may be along the lines of that utilized in U.S. Pat. No. 3,213,438, where the generation and reception of sonic signals between two transducers is shown. Another circuit for the detection of electrical conductivity is shown in U.S. Pat. 3,898,637.

Figure 2:
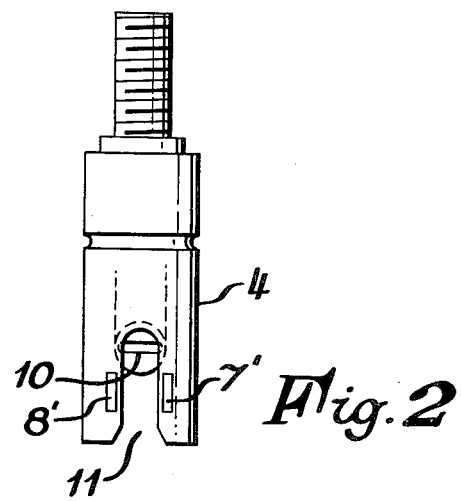
FIG. 2 shows a sectional view of another embodiment of the probe along, 'A' in FIG. 1.

The embodiment shown in FIG. 2 comprises probe 4 with gap 11 between light transmitter 7' and light receiver 8', through which gap 11 there is an orifice 10, through which the liquid flows. Suitable circuitry for measuring the transmission of light across the path between transmitter 7' and receiver 8' is shown in U.S. Pat. No. 3,441,737.

In operation, according to one of the embodiments of the present invention, the intermittent grabs of sample flow are directed through the shaped orifice 10 to bridge the narrow gap 11 between the ultrasonic crystal transmitter 7 and receiver crystal 8. This sets off a "sample flowing" signal. This is an intermittent signal present only when the grab is being taken, for having passed through the gap 11, which is then re-established, each grab sample flows off the detector probe and out through outlet 3 into the container. When the container 5 is full, the sample is no longer able to flow through outlet 3 into the container 5 and the gap 11 is therefore continually bridged. This sets off a continuous signal/alarm indicating to the operative that the sample container is full.

I claim:

1. A liquid flow indicating device for sensing intermittent liquid flow and adapted for mounting on a sample-collecting container and comprising a flow monitor mounted on top of the container, the flow monitor having means forming a chamber having an inlet for the entrance of liquid and an outlet spaced from said inlet for the flow of said liquid out of said chamber, said liquid flowing along a path defined at its beginning by said inlet and at its end by said outlet, a probe mounted intermediately along the path in said chamber and comprising an energy transmitter and an energy receiver in spaced apart relation within said chamber, said transmitter being disposed on the transversely opposite side of the liquid path from said receiver said transmitter and said receiver having a passageway therebetween which includes said path and which permits the flow of said liquid along said path and between said transmitter and said receiver, whereby the flow of liquid along said path alters the energy transmitted across the path from said transmitter to said receiver, and the outlet receiving the liquid from the chamber and communicating with the container to deliver the liquid to the container and drain the chamber when no liquid is delivered to the inlet, a signal being generated when liquid is in the chamber between the transmitter and the receiver to indicate the intermittent flow of liquid through the chamber and the filling of the container.

2. A device as set forth in claim 1, wherein said transmitter is a light energy transmitter and said receiver is a light energy receiver.

3. A device as set forth in claim 1, wherein said transmitter is an ultrasonic energy transmitter and said receiver is an ultrasonic energy receiver.

4. A device as set forth in claim 1, wherein said means forming said chamber comprise two parts, one part having a liquid-tight connection with the other but being separable from said other part, said one part having said inlet therein and said other part having said outlet therein.

5. A device as set forth in claim 1, wherein said device comprises a relief valve having an outlet directed outwardly of said device and said container and comprises a passageway extending from said valve to the interior of said container.

* * * * *